(12) United States Patent
Hashimoto et al.

(10) Patent No.: US 7,364,549 B2
(45) Date of Patent: Apr. 29, 2008

(54) PULSE WAVE MEASURING APPARATUS

(75) Inventors: Masao Hashimoto, Kyoto (JP);
Kazunobu Itonaga, Kyoto (JP);
Tomoki Kitawaki, Okayama (JP);
Kazuhisa Tanabe, Kyoto (JP); Ryo Fukui, Kadoma (JP); Hironori Sato, Moriyama (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 257 days.

(21) Appl. No.: 10/757,721

(22) Filed: Jan. 15, 2004

(65) Prior Publication Data

US 2004/0254484 A1  Dec. 16, 2004

(30) Foreign Application Priority Data

Jan. 24, 2003  (JP)  ............................. 2003-015625

(51) Int. Cl.
*A61B 5/02* (2006.01)
(52) U.S. Cl. .................. 600/500; 600/485; 600/490
(58) Field of Classification Search ............... 600/485, 600/500–503
See application file for complete search history.

(56) References Cited

U.S. PATENT DOCUMENTS

| 4,561,447 | A | * | 12/1985 | Kawamura et al. | ......... | 600/500 |
|---|---|---|---|---|---|---|
| 5,094,244 | A | | 3/1992 | Callahan et al. | | |
| 5,551,437 | A | * | 9/1996 | Lotscher | ...................... | 600/485 |
| 5,743,856 | A | * | 4/1998 | Oka et al. | ..................... | 600/493 |
| 6,344,025 | B1 | * | 2/2002 | Inagaki et al. | .............. | 600/490 |
| 6,447,456 | B1 | * | 9/2002 | Tsubata | ....................... | 600/455 |
| 6,491,647 | B1 | * | 12/2002 | Bridger et al. | .............. | 600/585 |
| 2002/0077558 | A1 | * | 6/2002 | Itonaga et al. | .............. | 600/490 |
| 2002/0120199 | A1 | | 8/2002 | Ogura et al. | | |

FOREIGN PATENT DOCUMENTS

| CN | 1320411 | 11/2001 |
|---|---|---|
| EP | 0 885 588 A1 | 6/1997 |
| JP | 09-140679 A | 11/1995 |

* cited by examiner

*Primary Examiner*—Robert L. Nasser, Jr.
*Assistant Examiner*—Karen E Toth
(74) *Attorney, Agent, or Firm*—Morrison & Foerster LLP (57) ABSTRACT

A pulse wave measuring apparatus is disclosed which is capable of measuring the pulse wave accurately in stable fashion and which can be reduced in size and integrated for an improved convenience. The pulse wave measuring apparatus comprises a sensor unit having a plurality of semiconductor pressure sensors, a fixing stand for fixing a living organism in position, a pressure cuff for pressing the semiconductor pressure sensors against the living organism, and a press operation control unit for controlling the press operation of the pressure cuff. The press operation control unit is arranged in the fixing stand.

10 Claims, 10 Drawing Sheets

PULSE WAVE MEASURING APPARATUS

BACKGROUND OF THE INVENTION

1. Field of the Invention

The present invention relates to a press-type pulse wave measuring apparatus for measuring the pulse wave by pressing a pressure sensitive part against a living organism, or in particular to a press-type pulse wave measuring apparatus having a fixing stand for fixing the living organism in position.

2. Description of the Related Art

A press-type pressure measuring apparatus for measuring the contact pressure with an object of measurement by pressing the particular object of measurement is generally known. An application of the press-type pressure measuring apparatus is a pulse wave measuring apparatus. In the pulse wave measuring apparatus, the pulse wave generated from the artery located at a comparatively shallow point under the skin of a living organism is measured by pressing a pressure sensitive part against the surface of a living organism. The press-type pulse wave measuring apparatus comprises a plurality of semiconductor pressure sensors using a distortion gauge or a diaphragm as a pressure sensitive part. Measuring the pulse wave of a subject using the pulse wave measuring apparatus of this type is critical for knowing the health of the subject.

Generally, the press-type pulse wave measuring apparatus comprises the pressure sensitive part described above, a pressure part for pressing a pressure sensitive part against a living organism, a signal processing unit for processing the signal output from the pressure sensitive part, and a pressure part control unit for controlling the pressure part. The pressure sensitive part, the pressure part and a part of the signal processing unit are arranged on a sensor unit mounted removably on the living organism, while the pressure part control unit and the remaining part of the signal processing unit are arranged on the body of a PC (personal computer) or the like connected to the sensor unit through a signal cable.

The pressure part is of two types. One is a pressure mechanism for pressing the pressure sensitive part against a living organism directly by moving the pressure sensitive part up and down using a drive motor, and the other is a pressure mechanism for pressing the pressure sensitive part against the living organism by expanding or contracting a pressure cuff arranged just above the pressure sensitive part and move the pressure sensitive part up and down using an expansion/contraction part. The former mechanism includes a pressure part such as a drive motor in the sensor unit, while the latter mechanism includes a pressure cuff in the sensor unit and an expansion/contraction part in an independent pressure source connected to the sensor unit through an air tube on the one hand and to the PC through a signal cable on the other hand.

The pulse wave measuring apparatus having the configuration described above, in which the signal cable and the air tube are laid between the sensor unit, the PC and the pressure source, cannot be easily handled or transported while at the same time limiting the motion of the subject. In view of this problem, a compact, integrated apparatus is under development taking the user convenience into consideration.

The Japanese Unexamined Utility Model Publication No. 64-43905 (patent document 1) discloses a blood pressure measuring apparatus comprising a pressure part as a pressure mechanism for moving a pressure sensitive part up and down directly using a drive motor, wherein a pressure sensitive part, a pressure part, a signal processing unit and a pressure part control unit are arranged in a sensor unit. This eliminates the PC and realizes the size reduction and integration of the apparatus.

The patent deference 1 also suggests a blood pressure measuring apparatus comprising a pressure cuff is used as a pressure part, and a pressure mechanism for moving the pressure sensitive part up and down by expanding/contracting the pressure cuff, wherein a sensor unit has arranged therein the pressure sensitive part, the pressure part, the signal processing unit and the pressure part control unit. This eliminates the need of the PC and the pressure source, thereby making possible the size reduction and integration of the apparatus.

On the other hand, Japanese Unexamined Utility Model Publication No. 3-67605 (patent document 2) discloses a pulse wave measuring apparatus capable of measuring the pulse wave accurately in stable fashion by fixing a living organism in position. The pulse wave measuring apparatus disclosed in this publication includes a fixing device for fixing the wrist in position, and has such a configuration that the sensor unit is mounted after the wrist of the subject is fixed in position using the fixing device. The use of this fixing device can fix the wrist in position in stable fashion, and therefore the sensor unit can be more accurately mounted just above the artery, thereby making it possible to measure the pulse wave accurately in stable fashion.

In the blood pressure measuring apparatus using the drive motor disclosed in patent document 1 described above, however, the pressure part is complicated, and the fact that the drive motor providing a power source is arranged in proximity to the signal processing unit poses the problem that a noise is superposed on the signal processing unit and the blood pressure is difficult to measure accurately in stable fashion. The pressure mechanism including the drive motor, on the other hand, poses the problem that since the direction in which the pressure sensitive part is moved up and down is uniquely determined, it is difficult to press the sensor surface uniformly against the body of a living organism having a curved surface, thereby making it difficult to measure the blood pressure accurately in stable fashion.

With the blood pressure measuring apparatus using a pressure cuff suggested in patent document 1, the sensor surface can be pressed uniformly against the body surface of a living organism, and as compared with the blood pressure measuring apparatus using a drive motor, the pulse wave can be measured accurately in stable fashion. With the pressure mechanism using the pressure cuff, however, the expansion/contraction part is indispensable, as explained above. The expansion/contraction part includes a pressure pump, a suction pump and a switching valve for switching the connection of the pumps to the pressure cuff. In the case where these component parts are arranged in a sensor unit removably mounted on a living organism, the sensor unit becomes both bulky and heavy and cannot be mounted in stable fashion on the living organism. As a result, the blood pressure cannot be actually measured in stable fashion with this apparatus.

SUMMARY OF THE INVENTION

Accordingly, it is an object of this invention to solve the problem points described above and provide a compact and convenient pulse wave measuring apparatus of an integrated configuration capable of measuring the pulse wave accurately in stable fashion.

According to this invention, there is provided a pulse wave measuring apparatus comprising a sensor unit, a living organism fixing device, a pressure part and a pressure part control unit, wherein the pulse wave is measured by pressing the pressure sensitive part of the sensor unit against the living organism with the pressure part while the living organism is fixed by the living organism fixing device. The living organism fixing device is a fixing part including a fixing stand for fixing the living organism in position. The pressure part is for pressing the pressure sensitive part against the living organism. The pressure part control unit is a part for controlling the pressure part and arranged on the fixing stand constituting a part of the living organism fixing device.

The use of the fixing stand makes it possible to fix the living organism securely in position thereby making it possible to measure the pulse wave accurately in stable fashion. Also, the provision of the pressure part control unit in the fixing stand reduces the size and weight of the sensor unit, which can thus be mounted in stable fashion on the living organism. Also, the provision of the pressure part control unit in the fixing stand integrates the apparatus and therefore improves the convenience including the operating ease and portability of the apparatus.

Preferably, the pulse wave measuring apparatus according to this invention further comprises an A/D converter for converting the analog signal output from the pressure sensitive part into a digital signal, which converter is mounted in the fixing stand.

As described above, the provision of the A/D converter constituting a part of the signal processing unit in the fixing stand prevents the noise from being superposed on the A/D converter by the operation of the pressure part, and therefore makes possible accurate and stable pulse wave measurement. This effect is especially conspicuous in the case where a drive motor is used as a pressure part. Also, since the sensor unit and the fixing stand can be located in comparative proximity to each other, the length of the signal cable required to connect the pressure sensitive part and the A/D converter is shortened. As a result, noises are superposed on the signal cable to a lesser degree, thereby making it possible to measure the pulse wave accurately in stable fashion. Also, the motion of the subject is not limited by the signal cable. Further, the provision of the A/D converter in the fixing table integrates the apparatus and therefore improves the convenience including the operating ease and portability of the apparatus.

Preferably, with the pulse wave measuring apparatus according to this invention, the sensor unit, for example, includes a plurality of pressure sensitive part in array, and a signal extraction unit for time-division multiplexing the signals output from the plurality of the pressure sensitive part.

As described above, in view of the fact that the signal extraction unit constituting a part of the signal processing unit is arranged in the sensor unit, the number of the signal cables connecting the sensor unit and the fixing stand can be reduced, thereby eliminating the likelihood of limiting the motion of the subject by the signal cables.

Preferably, with the pulse wave measuring apparatus according to this invention, the pressure part, for example, includes an expandable pressure cuff, and the pressure part control unit includes an expansion part for expanding/contracting the pressure cuff by filling/discharging a fluid in and out of the pressure cuff and an expansion part control unit for controlling the operation of the expansion part.

In the case where the pressure cuff is used as the pressure part, the pressure sensitive surface can be pressed uniformly against the living organism. In such a case, however, the expansion part and the expansion part control unit are required. By arranging the expansion part and the expansion part control unit in the fixing stand, a compact, integrated apparatus becomes possible, thereby contributing to an improved operability and portability of the apparatus. Also, since the sensor unit and the fixing stand can be configured in comparative proximity to each other, the length of the tube connecting the pressure part and the expansion part can be reduced. As a result, the motion of the subject is not limited.

Preferably, the pulse wave measuring apparatus according to the invention further comprises, for example, an arithmetic operation processing unit for arithmetically processing the signal output from the A/D converter, a display unit for outputting the result of the arithmetic operation obtained from the arithmetic operation unit, and an operating unit for receiving an input from an external source, wherein the arithmetic processing unit, the display unit and the operating unit are arranged in the fixing stand.

By arranging the arithmetic operation unit, the display unit and the operating unit in the fixing stand, both the size is reduced more for a higher integration of the apparatus. As a result, the convenience including the operability and the portability of the apparatus are remarkably improved.

Preferably, the pulse wave measuring apparatus according to the invention further comprises, for example, an arithmetic operation processing unit for arithmetically processing the signal output from the A/D converter, a display unit for outputting the result of the arithmetic operation obtained from the arithmetic operation unit, and an operating unit for receiving an input from an external source, wherein the arithmetic processing unit is arranged in the fixing stand, and the display unit and the operating unit are arranged on the sensor unit.

As described above, the provision of the arithmetic operation unit in the fixing stand and the provision of the display unit and the operating unit on the sensor unit makes possible both the size reduction and the integration of the apparatus even further. As a result, the convenience including the operability and the portability of the apparatus are remarkably improved.

Preferably, the pulse wave measuring apparatus according to the invention further comprises, for example, an arithmetic operation processing unit for arithmetically processing the signal output from the A/D converter, a display unit for outputting the result of the arithmetic operation obtained from the arithmetic operation processing unit, and an operating unit for receiving an input from an external source, wherein the arithmetic operation processing unit, the display unit and the operating unit are arranged on the sensor unit.

As described above, the provision of the arithmetic operation processing unit, the display unit and the operating unit on the sensor unit makes possible both the size reduction and the integration of the apparatus even further. As a result, the convenience including the operability and the portability of the apparatus are remarkably improved.

DESCRIPTION OF THE PREFERRED EMBODIMENTS

Embodiments of the invention are explained below with reference to the accompanying drawings. These embodiments represent a pulse wave measuring apparatus using the wrist as an object portion of a subject at which the pulse wave of the subject is measured.

First Embodiment

Figure 1:
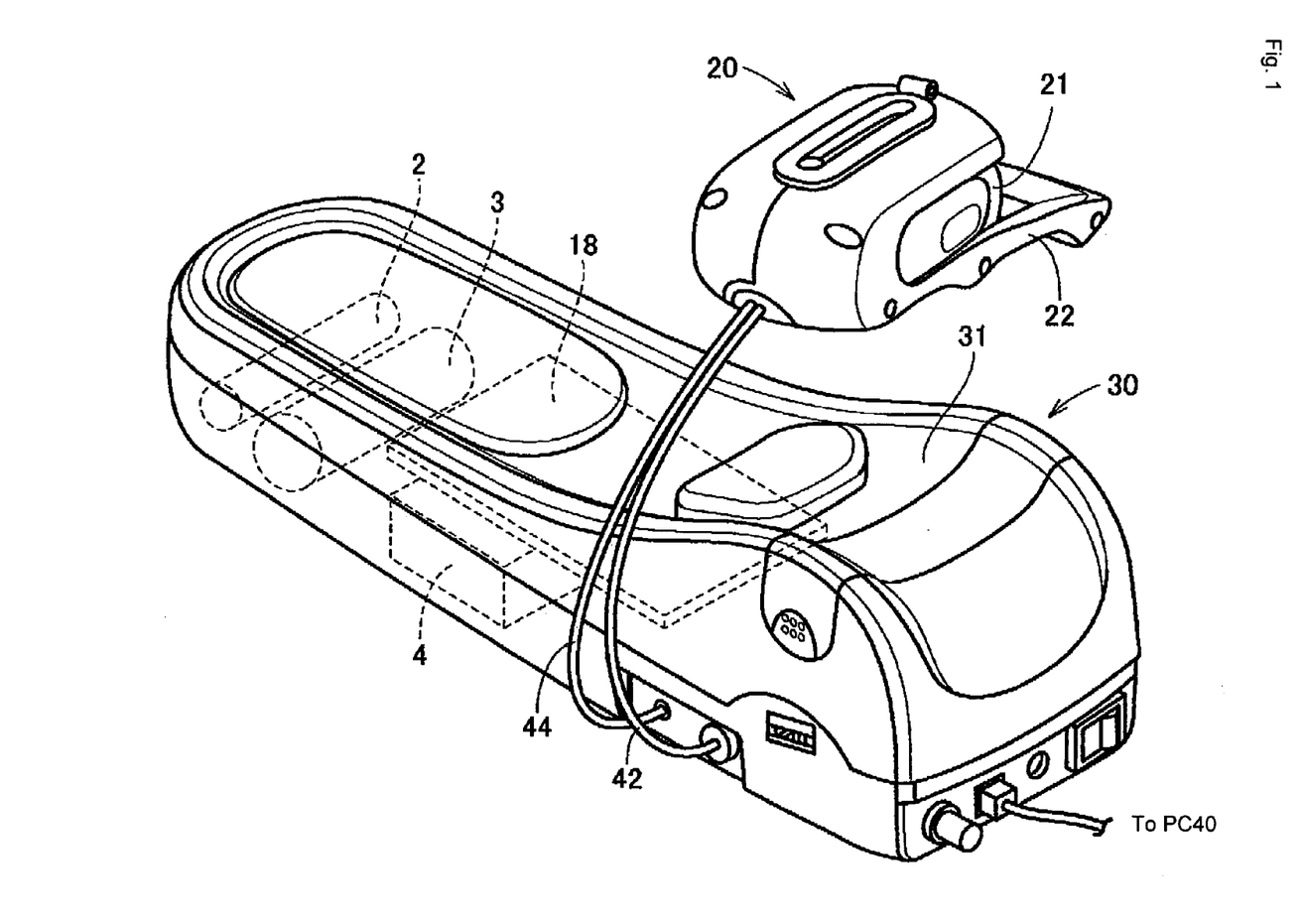
FIG. 1 shows a schematic perspective view of the structure of a pulse wave measuring apparatus according to a first embodiment of the invention.
Figure 2:
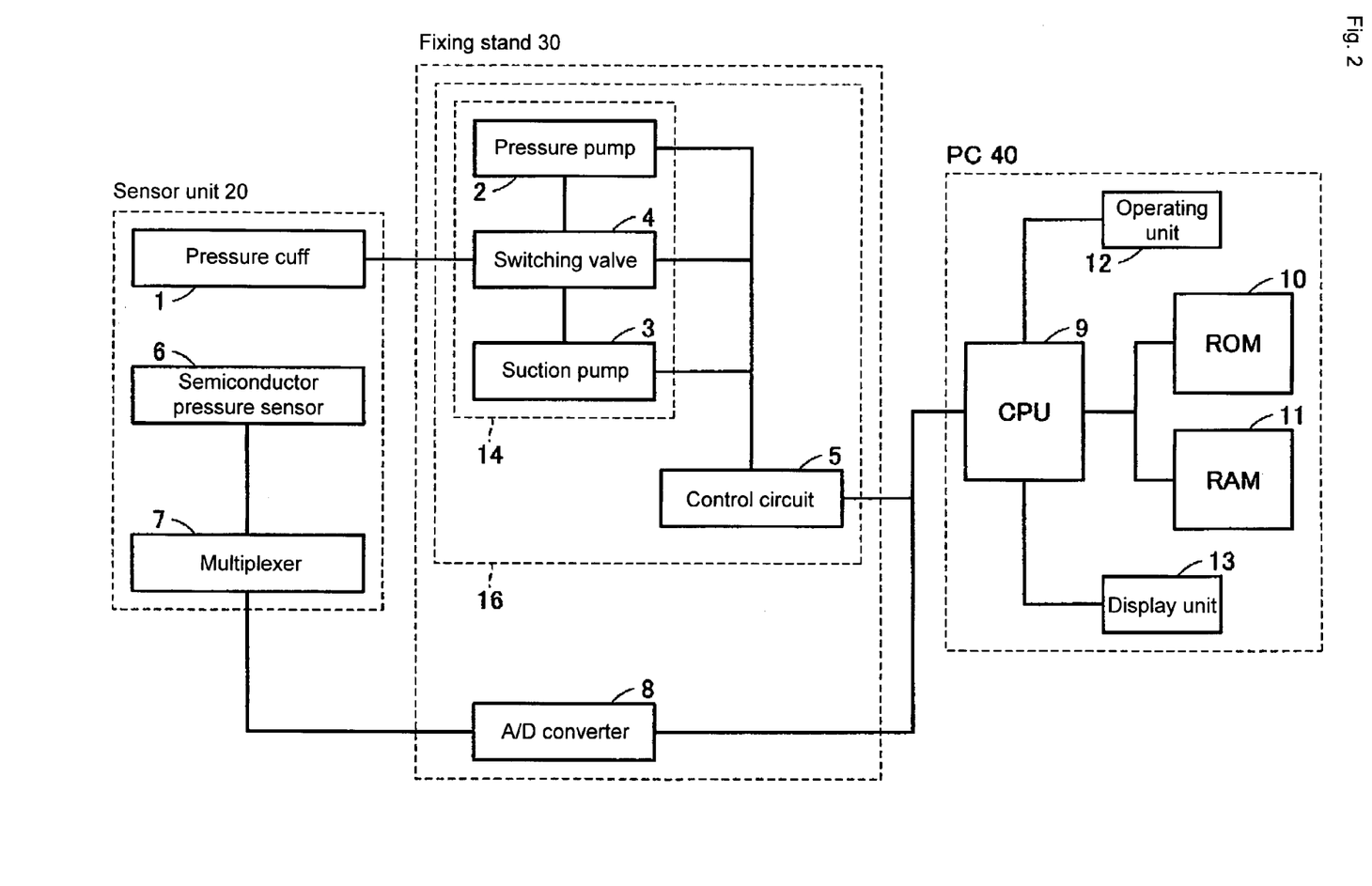
FIG. 2 shows a function block diagram of the configuration of a pulse wave measuring apparatus according to the first embodiment of the invention.
Figure 3:
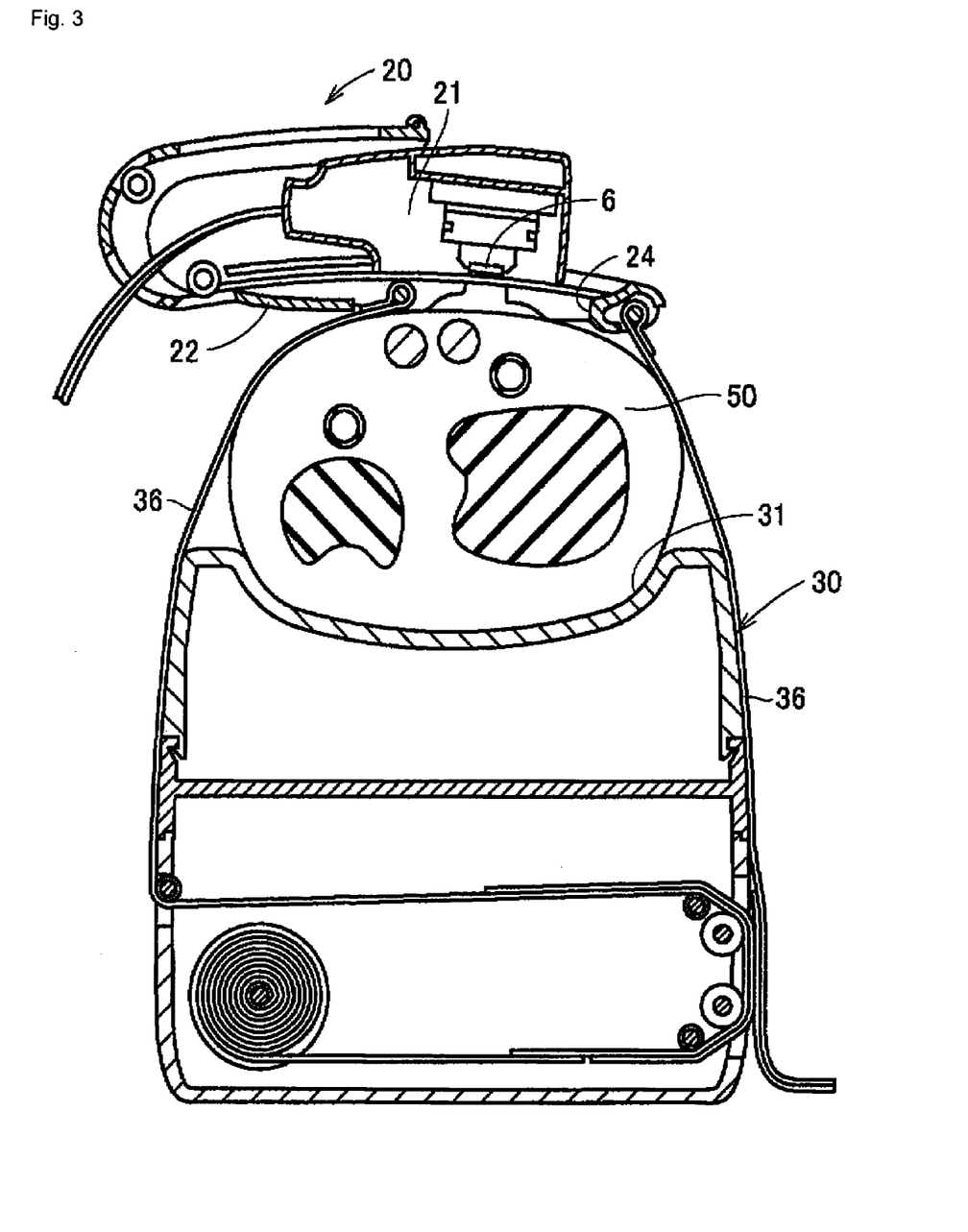
FIG. 3 shows a schematic sectional view of a state in which the pulse wave measuring apparatus according to the first embodiment of the invention is mounted on a living organism.
Figure 4:
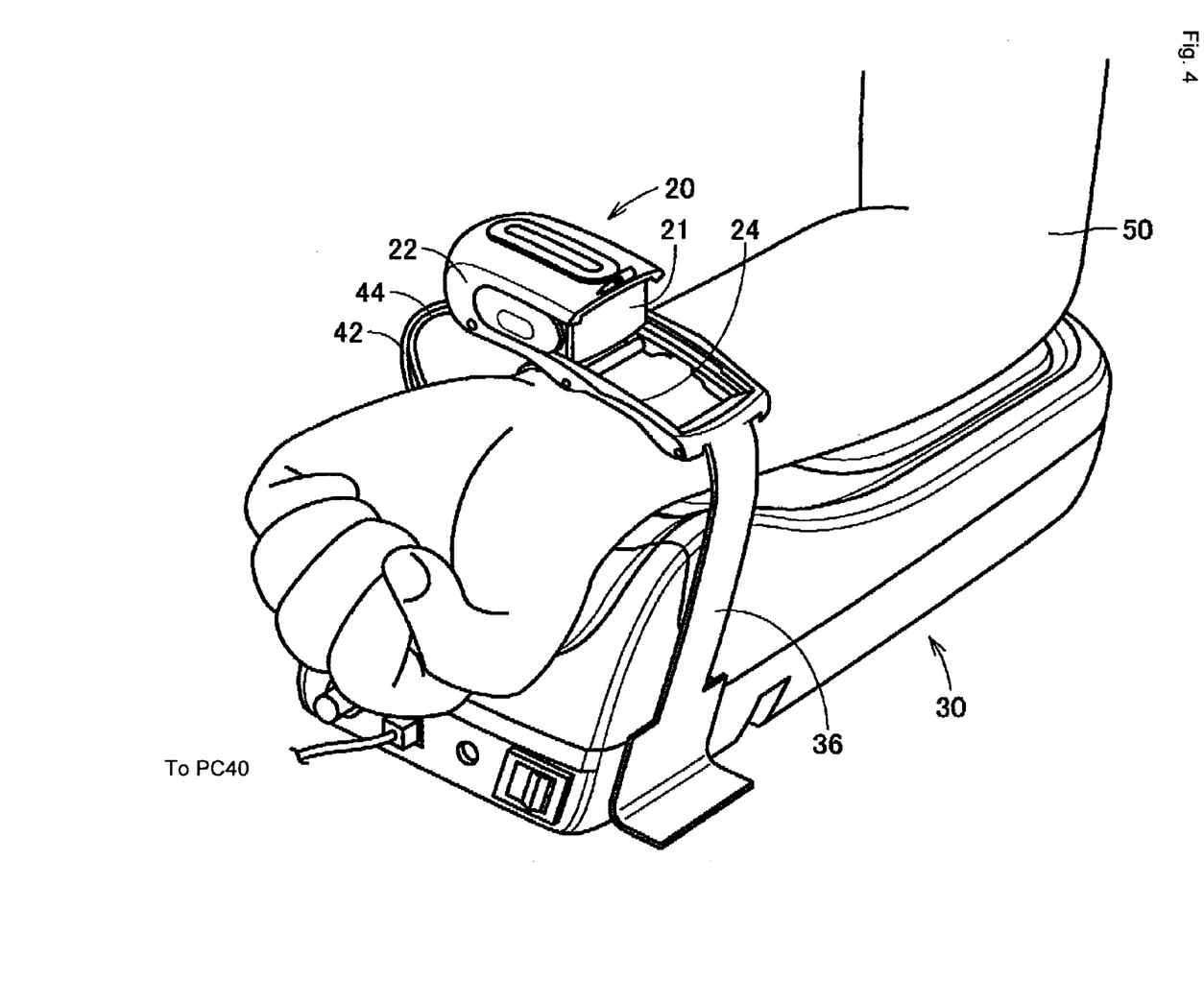
FIG. 4 shows a schematic perspective view of a state in which the pulse wave measuring apparatus according to the first embodiment of the invention is mounted on a living organism.
Figure 5:
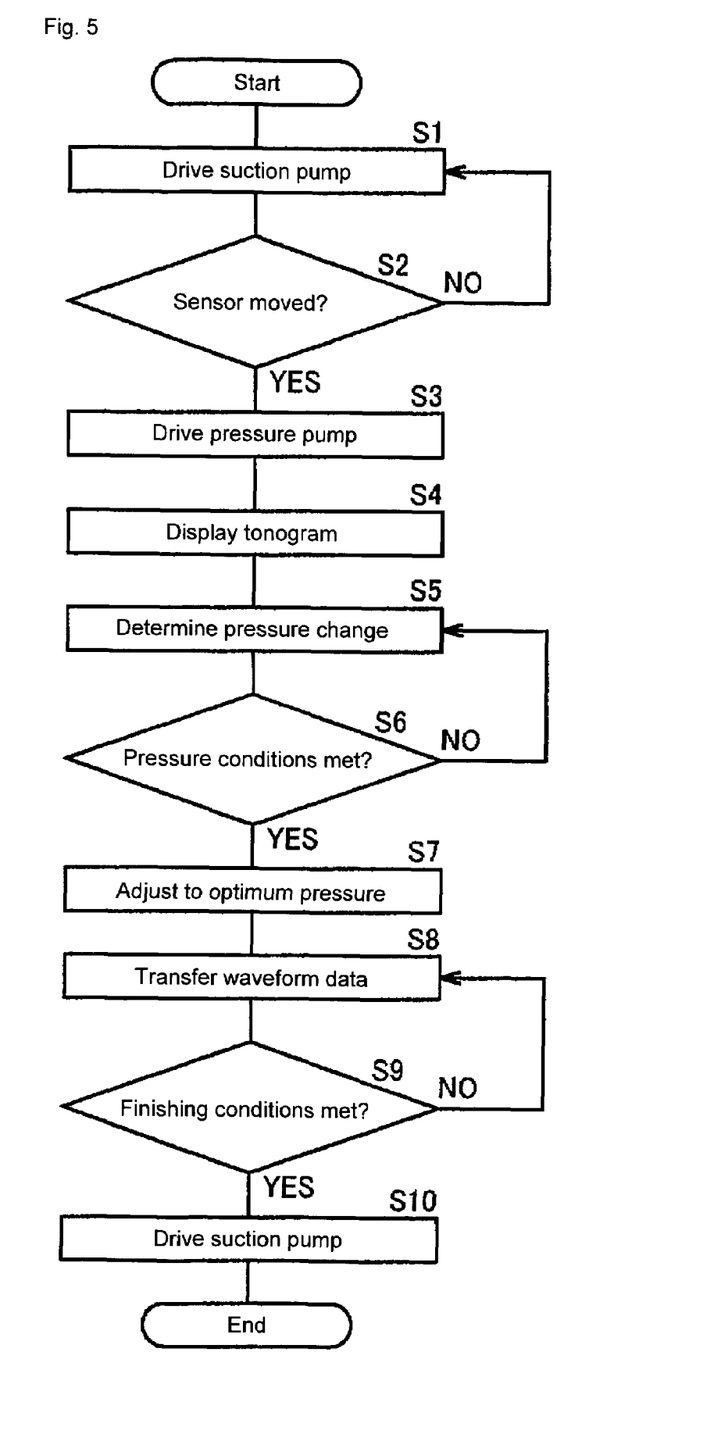
FIG. 5 shows a flowchart of the processing of the signal detected in the pulse wave measuring apparatus according to the first embodiment of the invention.

FIG. 1 is a perspective view schematically showing the structure of a pulse wave measuring apparatus according to a first embodiment of the invention. FIG. 2 is a function block diagram showing a configuration of the pulse wave measuring apparatus according to the first embodiment. FIGS. 3 and 4 are a sectional view and a perspective, respectively, schematically showing a state in which the pulse wave measuring apparatus according to this embodiment is mounted on a living organism. FIG. 5 is a flowchart showing the processing steps of measuring the pulse wave in the pulse wave measuring apparatus according to the first embodiment.

First, an external structure of the pulse wave measuring apparatus according to this embodiment is explained with reference to FIG. 1. As shown in FIG. 1, the pulse wave measuring apparatus according to this embodiment comprises a sensor unit 20 having a semiconductor pressure sensor 6 (FIGS. 2 and 3) constituting a pressure sensitive part, a fixing stand 30 for fixing a living organism in position, and a PC 40 not shown. The fixing stand 30 functions as a living organism fixing device for fixing the living object with fastening bands described later.

The sensor unit 20 includes a case 21 having the semiconductor pressure sensor 6 therein, and a base 22 for supporting the case 21 slidably. The case 21 has built therein a pressure cuff (not shown) as a pressure part. A semiconductor chip with the semiconductor pressure sensors 6 formed in array is assembled on the lower surface of the pressure cuff. The pressure cuff contracts/expands so that the semiconductor chip moves up/down in such a manner that the semiconductor pressure sensors 6 are pressed against the surface of the wrist at the time of measurement.

The fixing stand 30 is a box-like rest having on the upper surface thereof a depression 31 in which the arm extending from the elbow to the wrist of the subject can be placed. The fixing stand 30 contains a pressure pump 2, a suction pump 3 and a switching valve 4 as an expansion part 14 (FIG. 2). Further, a control board 18 is arranged in the fixing stand 30.

An input/output terminal is arranged on the front surface of the fixing stand 30. The control board 18 in the fixing stand 30 and a PC 40 are connected communicably with each other through a USB (universal serial bus) cable. The sensor unit 20 and the fixing stand 30 are connected to each other through a signal cable 42 and an air tube 44. The sensor unit 20 and the fixing stand 30 are also connected to each other by the flexible fastening bands 36 (FIGS. 3 and 4).

With reference to FIG. 2, the function blocks of the pulse wave measuring apparatus according to this embodiment are explained. As shown in FIG. 2, the sensor unit 20 includes a plurality of the semiconductor pressure sensors 6 having a diaphragm and a resistor bridge circuit for detecting the pulse pressure, a multiplexer 7 constituting a signal extraction unit for selectively extracting by time-division multiplexing a plurality of voltage signals output from the plurality of the semiconductor pressure sensors 6, and a pressure cuff 1 adjusted under pressure to press the semiconductor pressure sensors 6 against the wrist.

The fixing stand 30 includes a pressure pump 2 for generating an internal pressure (hereinafter referred to as the cuff pressure) of the pressure cuff 1, a suction pump 3 for reducing the pressure, a switching valve 4 for selectively switching the connection of the pressure pump 2 and the suction pump 3, a control circuit 5 constituting an expansion part control unit for controlling the operation of the pressure pump 2, the suction pump 3 and the switching valve 4, and an A/D converter 8 for converting the output signal from the sensor unit 20 into a digital data. Of these component parts, the control circuit 5 and the A/D converter 8 are formed or arranged on the control board 18 in the fixing stand 30. According to this embodiment, the pressure pump 2, the suction pump 3 and the switching valve 4 constituting the expansion part 14 and the control circuit 5 constituting the expansion part control unit make up a pressure part control unit 16 for controlling the pressure part.

The PC 40 includes a CPU (central processing unit) 9 as an arithmetic operation processing unit for executing the various arithmetic operations including the calculations to control the pulse wave measuring apparatus centrally, a ROM (read-only memory) 10 and a RAM (random access memory) 11 for storing the data and the program to control the pulse wave measuring apparatus, an operating unit 12 adapted to be operated externally to input the various information, and a display unit 13 having a LCD or the like for externally outputting various information including the result of pulse wave measurement.

With reference to FIGS. 3 and 4, the steps in which the subject mounts the pulse wave measuring apparatus having the aforementioned configuration are explained below. First, the portion of arm 50 extending from the elbow to the wrist is placed in the depression 31 formed in the upper surface of the fixing stand 30. In the process, as shown in FIGS. 3 and 4, care is taken to arrange the wrist of the subject in a position corresponding to the fastening band 36 led out of the fixing stand 30. In this way, the wrist of the subject is securely fixed in position by the fixing stand 30.

Next, the fastening band 36 is led out of the fixing stand 30 by a predetermined amount, and the sensor unit 20 is arranged to come to the position just above the wrist of the subject. At the same time, the position of the radial artery is checked by touch or the like, and the sensor unit 20 is arranged in position in such a manner that the center of an opening 24 formed in the base 22 comes substantially above the radial artery.

The forward end of the movable one of the fastening bands is attached to the side surface of the fixing stand 30 far from the side surface thereof by way of which the movable one of the fastening bands 36 is pulled out. Through the aforementioned steps, the mounted state of the apparatus is realized as shown in FIGS. 3 and 4.

In actual measurement of the pulse wave, the case 21 of the sensor unit 20 is slid to such a position as to close the opening 24 of the base 22. By adjusting the cuff pressure of the pressure cuff arranged above the semiconductor pressure sensors 6, the semiconductor pressure sensors 6 are moved down to the wrist through the opening 24 thereby to impart pressure. As a result, the pulse wave can be detected by the semiconductor pressure sensors 6.

The processing steps for measuring the pulse wave by the pulse wave measuring apparatus according to this embodiment are explained with reference to the flowchart of FIG. 5. The program according to this flowchart and the data accessed at the time of executing the program are stored beforehand in the ROM 10 or the RAM 11. The CPU 9, accessing the data appropriately, reads and executes the program. In this way, the process of measuring the pulse wave is executed.

First, the user turns on a power switch (not shown). The CPU 9 instructs the control circuit 5 to drive the suction pump 3. In compliance with this instruction, the control circuit 5 turns the switching valve 4 to the suction pump 3 side and drives the suction pump 3 (S1).

The suction pump 3, once driven, works to reduce the cuff pressure to a level sufficiently lower than the atmospheric pressure through the switching valve 4. Thus, the semiconductor pressure sensors 6 move upward in the sensor unit 20. As a result, the semiconductor pressure sensors 6 are prevented from being unnecessarily projected to cause a malfunction or a failure.

After that, the user mounts the sensor unit 20 on the wrist, for example, as shown in FIG. 4, and turns on a start button (not shown). The CPU 9 then determines whether the semiconductor pressure sensors 6 have moved or not, i.e. whether the case 21 of the sensor unit 20 has slid to a position above the surface of the wrist along a slide groove (S2). A microswitch not shown for detecting the sliding motion is arranged in the housing of the sensor unit 20, and based on the detection signal of the microswitch, the CPU 9 determines whether the semiconductor pressure sensors 6 have moved or not.

As long as it is not determined whether the semiconductor pressure sensors 6 have moved or not (NO in S2), the process of step S1 is repeated. Once it is determined that the semiconductor pressure sensors 6 have moved (YES in S2), however, the CPU 9 instructs the control circuit 5 to drive the pressure pump 2. In compliance with this instruction, the control circuit 5 turns the switching valve 4 to the pressure pump 2 side and drives the pressure pump 2 (S3). As a result, the cuff pressure increases and the semiconductor pressure sensors 6 move down toward the wrist and are pressed against the wrist surface.

Once the semiconductor pressure sensors 6 are pressed against the wrist surface, the pressure information in the form of a voltage signal from the semiconductor pressure sensors 6 is led out through a multiplexer 7, and after being converted into digital information by the A/D converter 8, is applied to the CPU 9. Using these digital information, the CPU 9 produces and displays a tonogram on the display unit 13 (S4).

Next, the CPU 9, in order to detect the pulse wave based on the pressure information input from the semiconductor pressure sensors 6, calculates the amount of change in pressure level due to the pressure cuff 1 and compares the calculated change amount with a predetermined change amount for which the pulse wave can be detected (S5). In the case where the comparison shows that the calculated change amount is covered by the predetermined change amount, it is determined that the cuff pressure conditions for pulse wave detection are met (YES in step S6). Otherwise, pressure continues to be imparted to the pressure cuff 1 by the pressure pump 2, while the steps S5 and S6 are repeated until the cuff pressure conditions are met.

Once the cuff pressured conditions are met (YES in S6), the pressure pump 2 is adjusted in such a manner that the optimum level of pressure for pulse wave detection is imparted to the semiconductor pressure sensors 6 due to the pressure cuff 1 (S7).

While pressure is adjusted to optimum level for the pressure cuff 1, the pressure information output from the semiconductor pressure sensors 6, i.e. the pulse waveform data of the radial artery are transferred to the CPU 9 through the multiplexer 7 and the A/D converter 8 (S8).

The CPU 9 receives the waveform data, and based on this data, detects the pulse wave. Before determination, after receipt of the waveform data, that the predetermined conditions for finishing the pulse wave detection are met, the pulse wave data transfer in step S8 is repeated. The process for pulse wave detection based on the received waveform data is executed in a well-known way, and therefore is not described in detail.

Once the predetermined conditions for finishing the pulse wave detection are met (YES in S9), the CPU 9 drives the suction pump 3 through the switching valve 4 (S10). As a result, the wrist is released from the pressure of the semiconductor pressure sensors 6, and thus the series of the pulse wave detection process is finished.

The CPU 9 outputs the detected pulse wave information through the display unit 13, etc. Alternatively, the pulse wave information may be used for calculating the AI (augmentation index) and outputting the calculated AI.

With the pulse wave measuring apparatus having the configuration described above, the living organism is fixed in position by use of the fixing stand 30. Thus, the pulse wave can be measured accurately in stable fashion. At the same time, the provision of the pressure pump 2, the suction pump 3, the switching valve 4 and the control circuit 5 in the fixing stand 30 reduces both the size and the weight of the sensor unit 20. Therefore, the sensor unit 20 can be mounted securely on the living organism. Also, since the A/D converter 8 is arranged in the fixing stand 30, the noise superimposed on the A/D converter 8 is reduced, thereby making it possible to measure the pulse wave accurately in stable fashion. Further, in this configuration, the apparatus can be reduced in size and integrated, thereby contributing to an improved convenience such as the handling ease and portability.

In addition, the distance between the sensor unit 20 and the fixing stand 30 can be kept comparatively small. Therefore, the length of the signal cable 42 connecting the semiconductor pressure sensors 6 and the A/D converter 8 is reduced, and so is the length of the air tube 44 connecting the pressure cuff 1 and the switching valve 4. As a result, the motion of the subject is not limited by the signal cable 42 or the air tube 44. Further, the noise superimposed on the signal cable 42 is remarkably reduced, and therefore the pulse wave can be measured accurately.

Furthermore, the aforementioned configuration reduces the number of the signal cables 42 connecting the sensor unit 20 and the fixing stand 30. Therefore, the motion of the subject is not limited by the signal cables 42.

Second Embodiment

Figure 6:
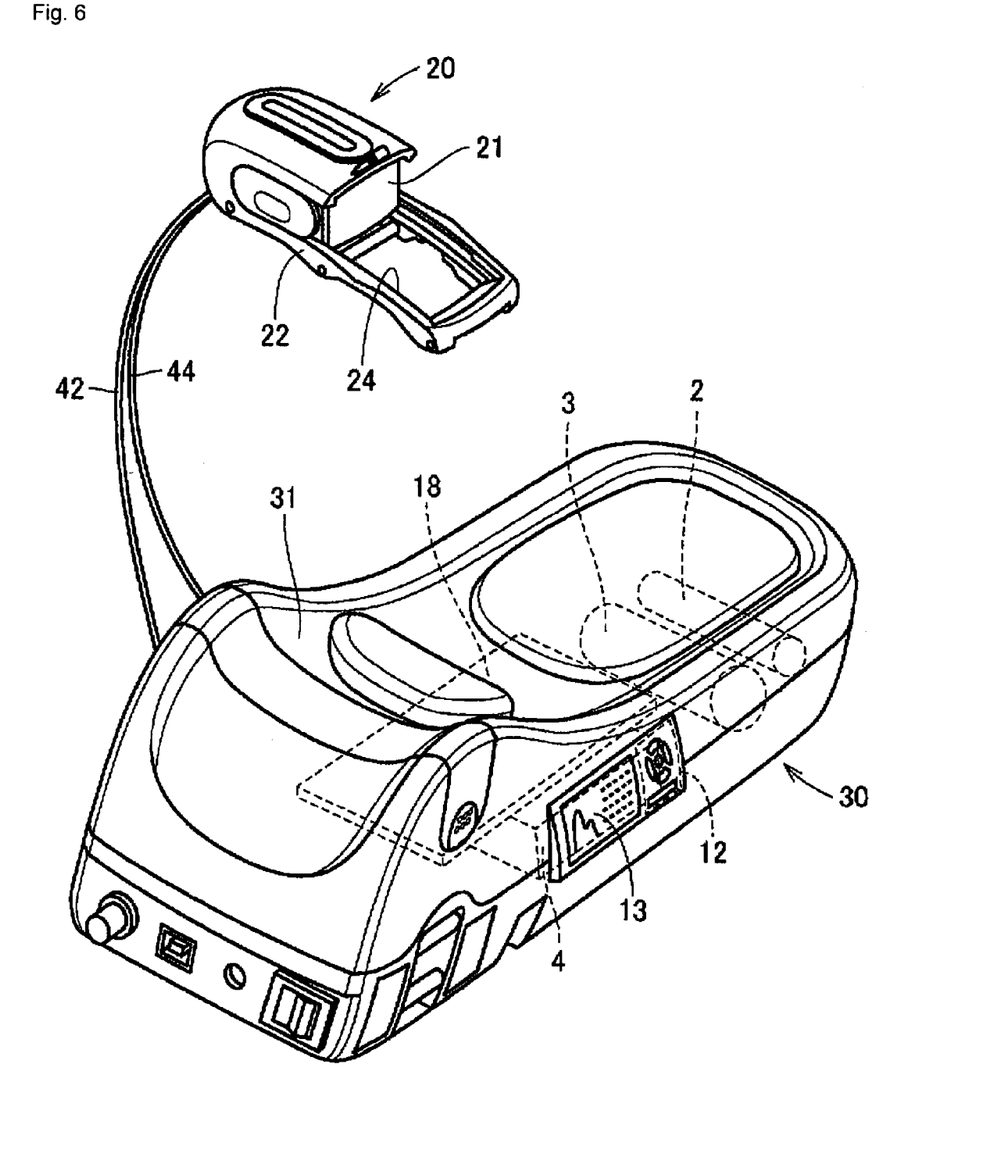
FIG. 6 shows a schematic perspective view of the structure of a pulse wave measuring apparatus according to a second embodiment of the invention.
Figure 7:
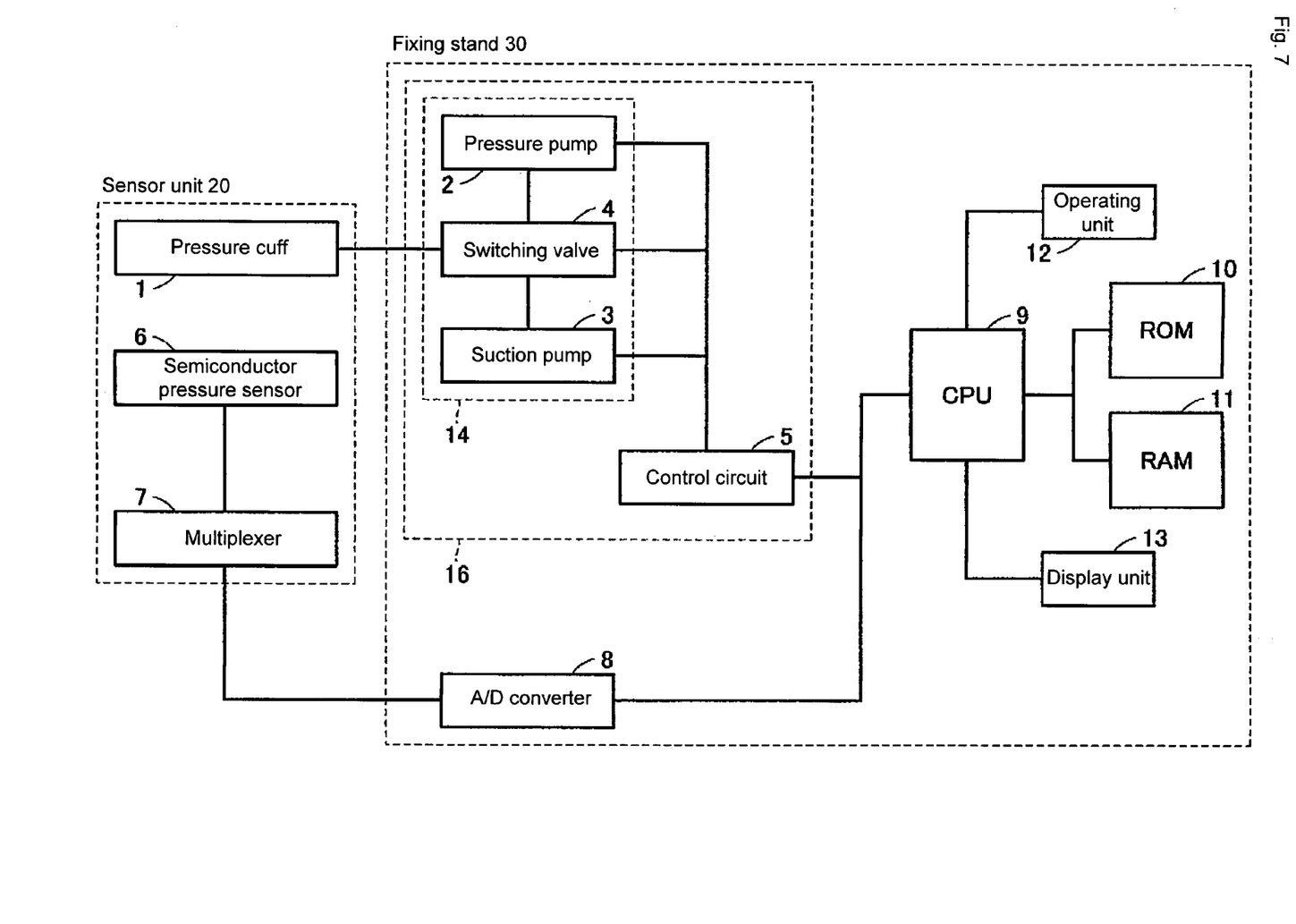
FIG. 7 shows a function block diagram of the configuration of a pulse wave measuring apparatus according to the second embodiment of the invention.

FIG. 6 is a perspective view schematically showing the structure of a pulse wave measuring apparatus according to a second embodiment of the invention. FIG. 7 is a function block diagram showing the configuration of the pulse wave measuring apparatus according to this embodiment. In this embodiment, the component parts identical or similar to the corresponding component parts in the first embodiment are designated by the same reference numerals, respectively, and not described again.

First, with reference to FIG. 6, the external structure of the pulse wave measuring apparatus according to this embodiment is explained. As shown in FIG. 6, the pulse wave measuring apparatus according to this embodiment comprises only a sensor unit 20 and a fixing stand 30, and unlike the first embodiment, comprises no PC. Also, in the pulse wave measuring apparatus according to this embodiment, an operating unit 12 and a display unit 13 are arranged on the side surface of the fixing stand 30.

Next, with reference to FIG. 7, the function blocks of the pulse wave measuring apparatus according to this embodiment are explained. As shown in FIG. 7, the sensor unit 20 includes a plurality of semiconductor pressure sensors 6, a multiplexer 7 for multiplexing by time division a plurality of voltage signals output from the semiconductor pressure sensors 6 and a pressure cuff 1 for pressing the semiconductor pressure sensors 6 against the wrist.

The fixing stand 30 includes a pressure pump 2 for imparting the cuff pressure, a suction pump 3 for reducing the pressure, a switching valve 4 for selectively switching the connection of the pressure pump 2 and the suction pump 3 to the air tube 44, a control circuit 5 for controlling the operation of the pressure pump 2, the suction pump 3 and the switching valve 4, an A/D converter 8 for converting the output signal from the sensor unit 20 to digital data, a CPU 9 for executing various processing operation including the arithmetic operation to centrally control the pulse wave measuring apparatus, a ROM 10 and a RAM 11 for storing the data and the program to control the pulse wave measuring apparatus, an operating unit 12 adapted to be externally manipulated to input various information, and a display unit 13 having a LCD, etc. for externally outputting various information such as the result of pulse wave detection. Of these component parts, the control circuit 5, the A/D converter 8, the CPU 9, the ROM 10 and the RAM 11 are formed or arranged on a control board 18 (FIG. 6) arranged in the fixing stand 30.

This configuration produces the effect of the first embodiment described above while at the same time eliminating the need of the PC, and therefore the apparatus is reduced in size and can be integrated. As a result, the handling ease and the portability of the apparatus are remarkably improved.

Third Embodiment

Figure 8:
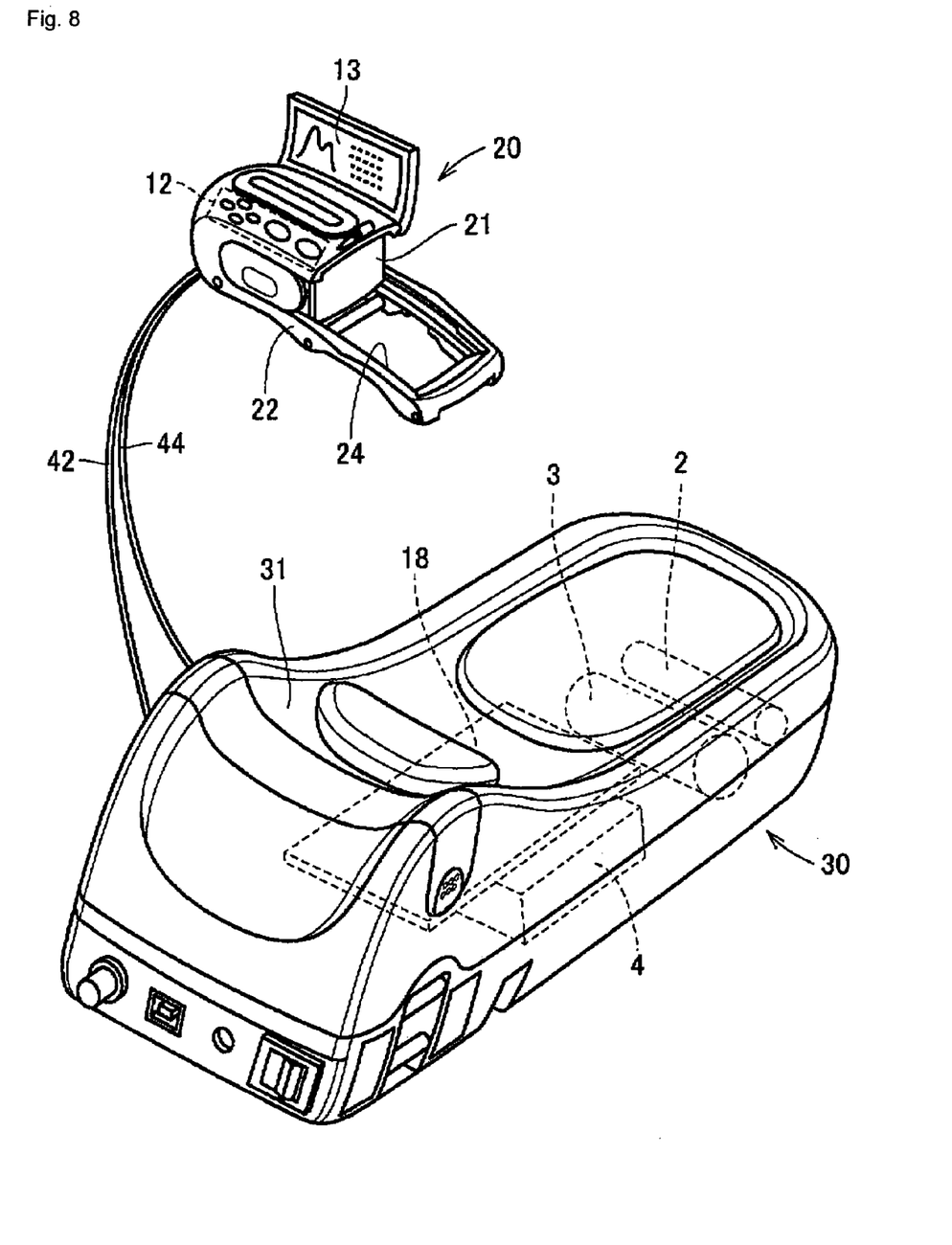
FIG. 8 shows a schematic perspective view of the structure of a pulse wave measuring apparatus according to a third embodiment of the invention.
Figure 9:
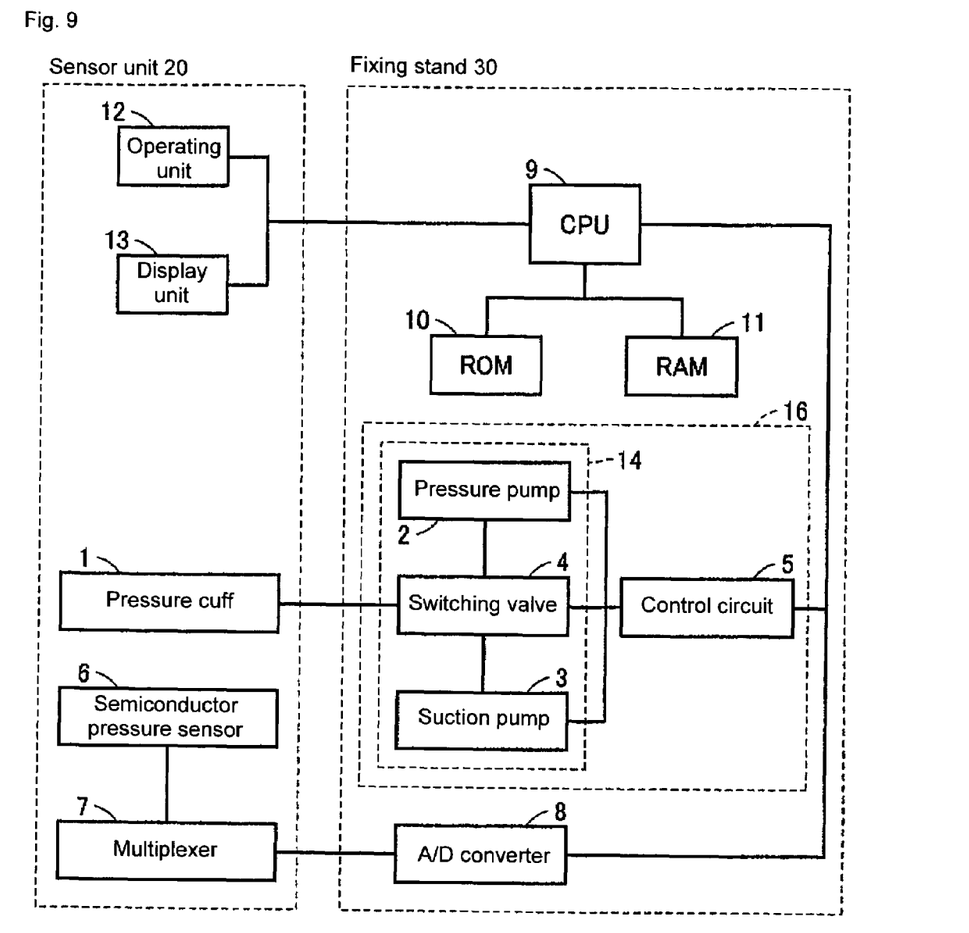
FIG. 9 shows a function block diagram of the configuration of a pulse wave measuring apparatus according to the third embodiment of the invention.

FIG. 8 is a perspective view schematically showing the structure of a pulse wave measuring apparatus according to a third embodiment of the invention. FIG. 9 is a function block diagram showing the configuration of a pulse wave measuring apparatus according to this embodiment. In this embodiment, the component parts identical or similar to the component parts of the first embodiment are designated by the same reference numerals, respectively, in the drawings and not described again.

First, with reference to FIG. 8, the external structure of the pulse wave measuring apparatus according to this embodiment is explained. As shown in FIG. 8, the pulse wave measuring apparatus according to this embodiment comprises only a sensor unit 20 and a fixing stand 30, but unlike the first embodiment, comprises no PC. Also, in the pulse wave measuring apparatus according to this embodiment, the sensor unit includes an operating unit 12 and a display unit 13.

Next, with reference to FIG. 9, the function blocks of the pulse wave measuring apparatus according to this embodiment are explained. As shown in FIG. 9, the sensor unit 20 includes a plurality of semiconductor pressure sensors 6, a multiplexer 7 for multiplexing by time division a plurality of voltage signals output from the semiconductor pressure sensors 6, a pressure cuff 1 for pressing the semiconductor pressure sensors 6 against the wrist, and the operating unit 12 adapted to be manipulated externally to input various information, and the display unit 13 having a LCD or the like for externally outputting various information such as the result of pulse wave detection.

The fixing stand 30 includes a pressure pump 2 for imparting the cuff pressure, a suction pump 3 for reducing the pressure, a switching valve 4 for selectively switching the connection of the pressure pump 2 and the suction pump 3 to the air tube 44, a control circuit 5 for controlling the operation of the pressure pump 2, the suction pump 3 and the switching valve 4, an A/D converter 8 for converting the output signal from the sensor unit 20 to digital data, a CPU 9 for executing various processing operation including the arithmetic operation to centrally control the pulse wave measuring apparatus, and a ROM 10 and a RAM 11 for storing the data and the program to control the pulse wave measuring apparatus. Of these component parts, the control circuit 5, the A/D converter 8, the CPU 9, the ROM 10 and the RAM 11 are formed or arranged on a control board 18 (FIG. 6) in the fixing stand 30.

This configuration produces the effect of the first embodiment described above while at the same time eliminating the need of the PC, and therefore the apparatus is further reduced in size and integrated. As a result, the handling ease and the portability of the apparatus are remarkably improved.

Fourth Embodiment

Figure 10:
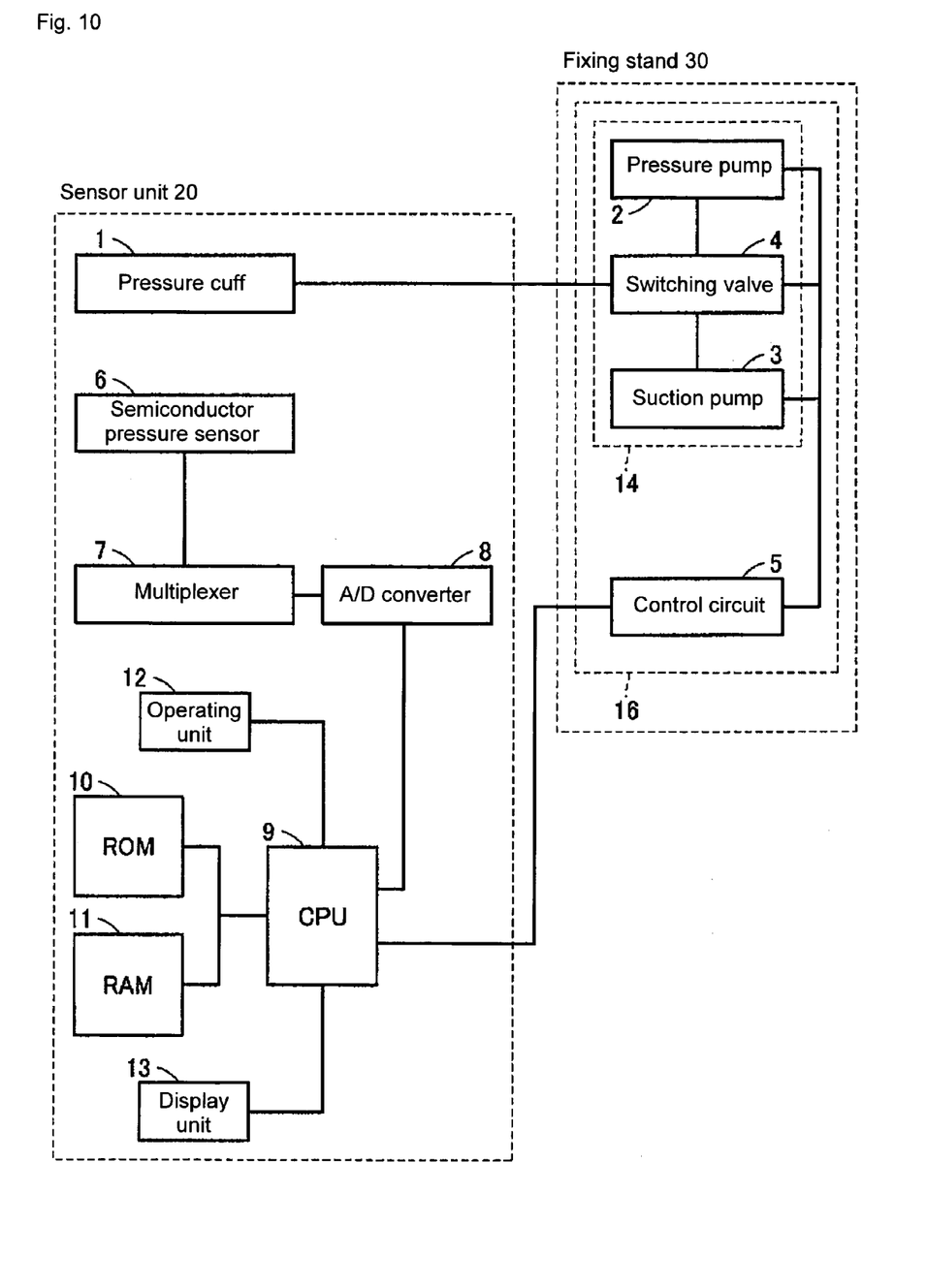
FIG. 10 shows a function block diagram of the configuration of a pulse wave measuring apparatus according to a fourth embodiment of the invention.

FIG. 10 is a function block diagram showing the configuration of a pulse wave measuring apparatus according to a fourth embodiment. In this embodiment, the component parts identical or similar to the component parts of the first embodiment are designated by the same reference numerals, respectively, in the drawings and not described again.

With reference to FIG. 10, the function blocks of the pulse wave measuring apparatus according to this embodiment is explained. As shown in FIG. 10, the sensor unit 20 includes a plurality of semiconductor pressure sensors 6, a multiplexer 7 for multiplexing by time division a plurality of voltage signals output from the semiconductor pressure sensors 6, a pressure cuff 1 adjusted for pressing the semiconductor pressure sensors 6 against the wrist, an A/D converter 8 for converting the output signal from the sensor unit to digital data, a CPU 9 for executing various processing operation including the arithmetic operation to centrally control the pulse wave measuring apparatus, a ROM 10 and a RAM 11 for storing the data and the program to control the pulse wave measuring apparatus, an operating unit 12 adapted to be externally manipulated to input various information, and a display unit 13 such as a LCD to externally output various information including the result of pulse wave detection.

The fixing stand 30 includes a pressure pump 2 for imparting the cuff pressure, a suction pump 3 for reducing the pressure, a switching valve 4 for switching the connection of to the pressure pump 2 and the suction pump 3 selectively to the air tube 44, and a control circuit 5 for controlling the operation of the pressure pump 2, the suction pump 3 and the switching valve 4. Of these component parts, the control circuit 5 is formed on a control board 18 (FIG. 8) arranged in the fixing stand 30.

The external structure of the pulse wave measuring apparatus according to this embodiment is similar to that of the pulse wave measuring apparatus according to the third embodiment.

This configuration produces the effect of the first embodiment described above while at the same time eliminating the need of the PC, and therefore the apparatus is further reduced in size and integrated. As a result, the handling ease and the portability of the apparatus are remarkably improved.

In the first to fourth embodiments described above, the pressure cuff is used as the pressure part. However, the invention is not specifically limited to such a pressure part, but of course applicable to the pulse wave measuring apparatus employing a drive motor as a pressure part.

Also, in the first to fourth embodiments described above, the pulse wave measuring apparatus using the wrist as object portion is illustrated. The invention, however, is not limited to such a pulse wave measuring apparatus but of course applicable with equal effect to a pulse wave measuring apparatus employing the upper arm or a finger as an object portion.

Each embodiment disclosed above is illustrative but not limitative in all points. The technical scope of this invention is defined by the claims appended hereto and includes all modifications without departing from the scope and spirit of the invention.

It will thus be understood from the foregoing description that according to this invention, there is provided a pulse wave measuring apparatus which is capable of measuring the pulse wave accurately in stable fashion on the one hand and which can be reduced in size and integrated on the other.

What is claimed is:

1. A pulse wave measuring apparatus comprising:
    a fixing stand adapted for fixing a living organism in position;
    a sensor unit movable with respect to the fixing stand and adapted to be positioned on the living organism when the living organism is positioned on the fixing stand, the sensor unit comprising at least one pressure sensitive part and a pressure part for pressing the at least one pressure sensitive part against the living organism positioned on the fixing stand;
    a fastening band connecting the fixing stand and the sensor unit for fixing the living organism between the fixing stand and the sensor unit; and
    a pressure part control unit for controlling the pressure part, characterized in that the pressure part control unit is disposed in the fixing stand and is in contact with the living organism when the fastening band fixes the living organism between the fixing stand and the sensor unit.

2. The pulse wave measuring apparatus according to claim 1, further comprising an A/D converter for converting the analog signal output from the pressure sensitive part to a digital signal,
    wherein the A/D converter is arranged in the fixing stand.

3. The pulse wave measuring apparatus according to claim 2,
    wherein the sensor unit includes a plurality of pressure sensitive part in array,
    the apparatus further comprising a signal extraction unit for multiplexing by time division the signal output from the plurality of the pressure sensitive part,
    wherein the signal extraction unit is arranged in the sensor unit.

4. The pulse wave measuring apparatus according to claim 3,
    wherein the pressure part includes an expandable pressure cuff, and
    wherein the pressure part control unit includes an expansion part for expanding/contracting the pressure cuff by filling/discharging a fluid into/from the pressure cuff, and an expansion part control unit for controlling the operation of the expansion part.

5. The pulse wave measuring apparatus according to any one of claims 2, 3 or 4, further comprising an arithmetic operation processing unit for arithmetically processing the signal output from the A/D converter, a display unit for outputting the result of arithmetic operation obtained from the arithmetic operation processing unit and an operating unit for receiving an input from an external source,
    wherein the arithmetic operation processing unit, the display unit and the operating unit are arranged in the fixing stand.

6. The pulse wave measuring apparatus according to any one of claims 2, 3 or 4, further comprising an arithmetic operation processing unit for arithmetically processing the signal output from the A/D converter, a display unit for outputting the result of arithmetic operation obtained from the arithmetic operation processing unit and an operating unit for receiving an input from an external source,
    wherein the arithmetic operation processing unit is arranged in the fixing stand, and the display unit and the operating unit are arranged on the sensor unit.

7. The pulse wave measuring apparatus according to any one of claims 2, 3 or 4, further comprising an arithmetic operation processing unit for arithmetically processing the signal output from the A/D converter, a display unit for outputting the result of arithmetic operation obtained from the arithmetic operation processing unit and an operating unit for receiving an input from an external source, wherein the arithmetic operation processing unit, the display unit and the operating unit are arranged in the sensor unit.

8. The pulse wave measuring apparatus according to claim 4, wherein the expansion part comprises:

an expansion device for expanding the pressure cuff;

a contraction device for contracting the pressure cuff; and a switching mechanism for switching operation between the expansion device and the contraction device in response to a signal from the expansion part control unit.

9. The pulse wave measuring apparatus according to claim 1, wherein the sensor unit further comprises a support for movably positioning the at least one pressure sensitive part and the pressure part on the living organism.

10. The pulse wave measuring apparatus according to claim 3, wherein the signal extraction unit comprises a multiplexer.

* * * * *